United States Patent [19]

Wellner et al.

[11] 4,413,985
[45] Nov. 8, 1983

[54] HYDROCEPHALIC ANTENATAL VENT FOR INTRAUTERINE TREATMENT (HAVIT)

[75] Inventors: Edward Wellner, Fairfax, Va.; Maria Michejda, Rockville; Gary D. Hodgen, Potomac, both of Md.

[73] Assignee: The United States of America as represented by the Dept. of Health & Human Services, Washington, D.C.

[21] Appl. No.: 325,730

[22] Filed: Nov. 30, 1981

Related U.S. Application Data

[63] Continuation-in-part of Ser. No. 298,773, Sep. 2, 1981, abandoned.

[51] Int. Cl.³ .............................................. A61M 27/00
[52] U.S. Cl. ...................................... 604/9; 604/247; 604/268; 604/264; 128/1 R
[58] Field of Search ................... 128/350 V, 274, 347, 128/218 NV, 748, 1 R, 200.26, 305.3, 207.16, 348, DIG. 26, 133; 137/539; 27/21, 24 A; 3/1.5; 604/8-10, 247, 264, 268

[56] References Cited

U.S. PATENT DOCUMENTS

| | | | |
|---|---|---|---|
| 2,670,735 | 3/1954 | Brody | 128/133 |
| 2,865,398 | 12/1958 | Popovich | 137/539 |
| 3,127,894 | 4/1964 | Smith | 128/347 |
| 3,288,142 | 11/1966 | Hakim | 128/350 V |
| 3,298,372 | 1/1967 | Feinberg | 604/8 |
| 3,371,352 | 3/1968 | Siposs et al. | 3/1.5 |
| 3,540,451 | 11/1970 | Zeman | 604/8 X |
| 3,674,050 | 7/1972 | Kuffer et al. | 128/350 V |
| 3,692,029 | 9/1972 | Adair | 128/347 X |
| 3,807,432 | 4/1974 | Cain | 137/539 X |
| 3,889,687 | 6/1975 | Harris et al. | 128/350 V |
| 4,164,943 | 8/1979 | Hill et al. | 128/348 |
| 4,340,037 | 7/1982 | Lewicky | 128/1 R |

FOREIGN PATENT DOCUMENTS

| | | | |
|---|---|---|---|
| 1151350 | 7/1963 | Fed. Rep. of Germany | 128/350 V |
| 7801416 | 9/1978 | Netherlands | 128/748 |

OTHER PUBLICATIONS

Bondarev et al., "Apparatus for Spraying Drugs Inside Cavities" Biomed. Eng. (U.S.A.), vol. 12, No. 5, (Sep.-Oct. 1978), Published: May, 1979.

*Primary Examiner*—Richard J. Apley
*Assistant Examiner*—Michelle N. Lester
*Attorney, Agent, or Firm*—Browdy and Neimark

[57] ABSTRACT

A hydrocephalic drainage valve consisting of a hollow shank with a pointed conical tip. The shank has an intake port adjacent the conical tip. A ball check valve in the shank is urged by a coiled spring toward closing relationship with the port. A hollow set screw is adjustably mounted in the shank to vary the biasing force on the valve ball. In one form, for manual implantation, a sleeve is slidably mounted on the shank, has a centrally apertured enlarged head and has implantation enlarged threads near the head. The head has aligned opposite radial grooves which are engageable by a manual insertion tool. In other forms, for pneumatic insertion, the shank has an enlarged head, employed as a driving piston in a pneumatic insertion tube. A washer member with implantation barbs is slidably mounted on the shank and is arranged to be locked to the shank subjacent the head responsive to the pneumatic driving action, with its barbs embedded in the fetal skin around the implantation puncture, thus holding the shank in operating position with the intake port exposed in the cranial vault.

15 Claims, 14 Drawing Figures

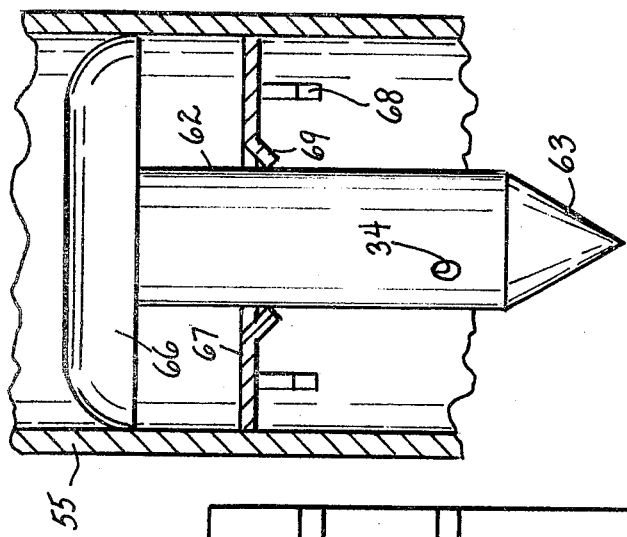
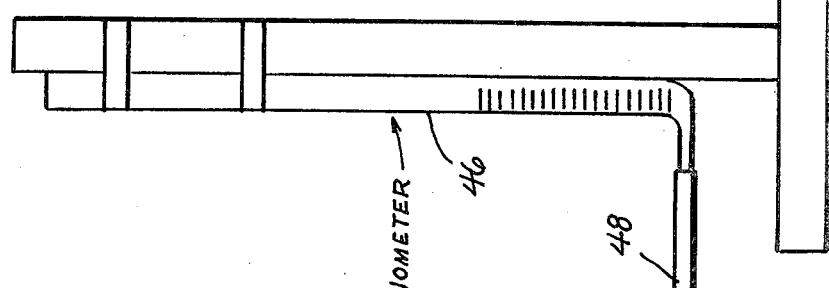
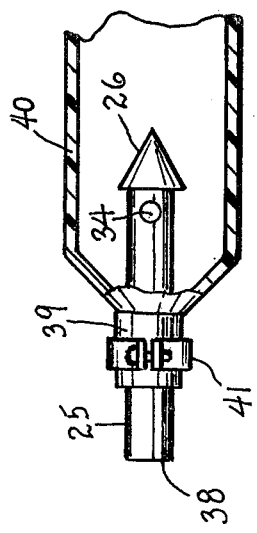

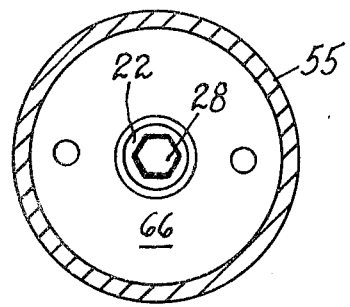
FIG. 11
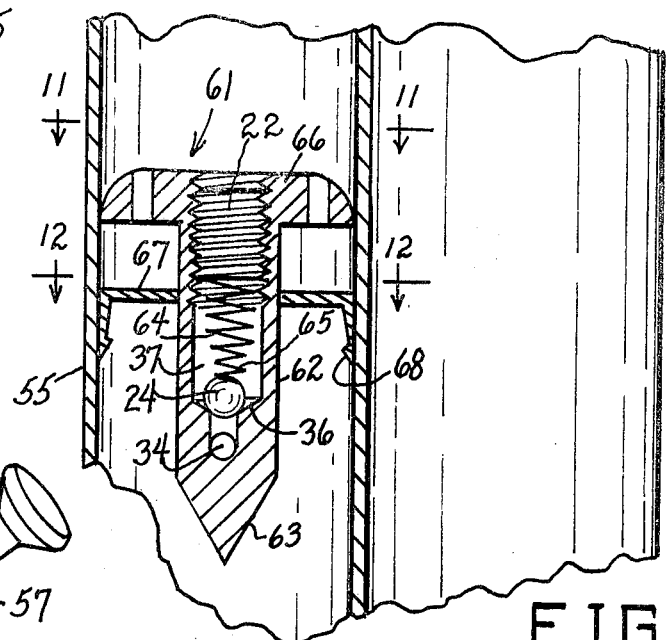
FIG. 10
FIG. 12
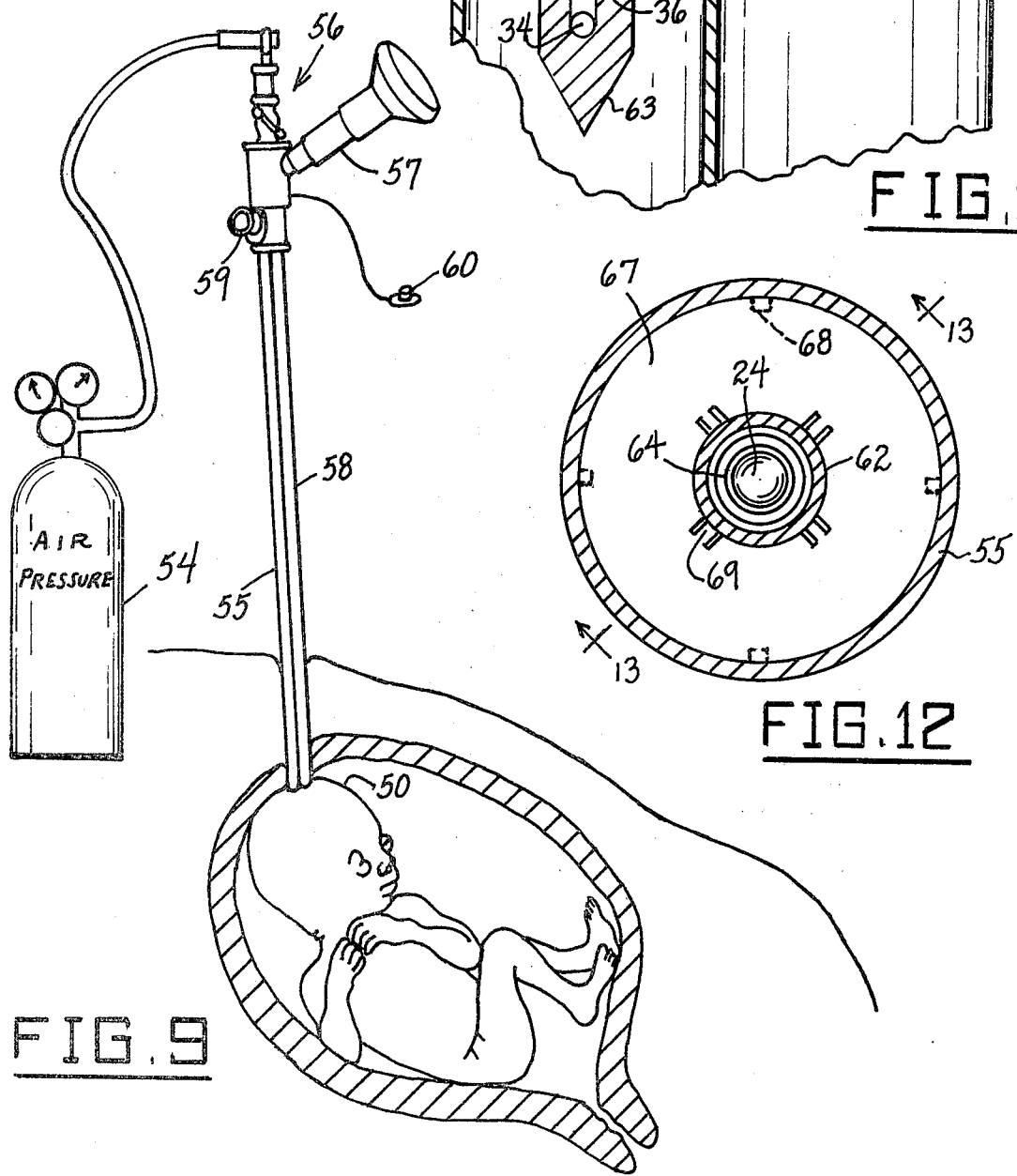
FIG. 9

HYDROCEPHALIC ANTENATAL VENT FOR INTRAUTERINE TREATMENT (HAVIT)

This is a continuation-in-part of our U.S. patent application Ser. No. 298,773, filed Sept. 2, 1981, now abandoned incorporated by reference.

FIELD OF THE INVENTION

This invention relates to surgical devices designed for the draining of cerebrospinal fluid, and more particularly to an indwelling valve for in-utero treatment of hydrocephalic fetuses.

BACKGROUND OF THE INVENTION

There are many prior art devices relating to various types of valves permitting the drainage of fluid for the treatment of hydrocephalus. However, these prior art devices are all used for the treatment of the already born, and are not suitable for the treatment of a hydrocephalic fetus. Examples of such prior art devices are shown in the following prior U.S. patents, found as a result of a preliminary search:

Holter et al, U.S. Pat. No. 2,969,066, Schwartz, U.S. Pat. No. 3,109,429, Hakim, U.S. Pat. No. 3,288,142, Kuffer et al, U.S. Pat. No. 3,674,050, Hakim, U.S. Pat. No. 3,924,635, Hakim, U.S. Pat. No. 4,106,510, and Hildebrandt et al, U.S. Pat. No. 4,156,422.

SUMMARY OF THE INVENTION

The present invention comprises prosthesis and devices for the treatment of the hydrocephalic fetus. It involves a prosthesis suitable for non-traumatic surgical placement or implantation in the fetus, while still in the womb. A particularly unique feature derives from its avoidance of extensive surgery for placement of existing prosthesis in "born" children or adults, where the shunt assembly vents cerebrospinal fluid (CSF) into the thoracic or abdominal cavity. Another highly important feature is the prevention of permanent brain damage and physical malformation to the fetus, which otherwise would be caused by the untreated intrauterine growth of a hydrocephalic fetus.

A particular problem resulting to the treatment of the unborn fetus is its relative inaccesibility in utero. A device according to the present invention can be used under conditions providing the barest access to the unborn fetus at fetoscopy. In contrast, existing prostheses for treating fetal hydrocephalus risk far more extensive uterine trauma, making premature labor, delivery and fetal death a likely sequel.

A hydrocephalic drainage valve according to one embodiment of the present invention consists of a hollow shank with a pointed enlarged conical tip, forming a shoulder. The shank has an intake port adjacent the shoulder. A ball check valve in the shank is urged by a coiled spring toward closing relationship with the port. A hollow set screw is adjustable in the shank to vary the biasing force on the ball. A sleeve is slidably engaged on the shank, extends adjacent the shoulder, has a centrally apertured head, and has implantation threads near the head. The head has aligned opposite radial grooves, or equivalent recess structure, engageable by an insertion tool. In other embodiments, the valve is adapted to be inserted by fluid pressure means and to be held in place by fetal skin-penetrating washer means carried on and lockingly engageable with the hollow valve shank, avoiding the use of implantation threads.

The invention is described in more detail in the attached articles by Hodgen entitled "Antenatal Diagnosis and Treatment of Fetal Skeletal Malformations with Emphasis on In Utero Surgery for Neural Tube Defects and Limb Bud Regeneration", and Michejda et al, entitled "In Utero Diagnosis and Treatment of Fetal Skeletal Anomalies: I—Hydrocephalus", both published in Volume 246, No. 10, 1981 issued of the Journal of the American Medical Association, pages 1079-1083 and 1093-1097, respectively. The contents of these two attached articles are incorporated by reference.

Accordingly, a main object of the invention is to provide a novel and improved method and apparatus for the treatment of the hydrocephalic fetus, which overcome the deficiencies and disadvantages of the prior known hydrocephalus treatments.

A further important object of the present invention is to provide an improved drainage valve device for the in utero treatment of a hydrocephalic fetus, said device being relatively easy to calibrate, being safe to use, and being usable even under conditions providing the barest access to the fetus at fetoscopy.

A still further object of the invention is to provide an improved technique and apparatus for treating hydrocephalus in a fetus by implanting a suitably calibrated cerebrospinal fluid drainage valve in the skull of the fetus to relieve hydrocephalic pressure and thereby to prevent permanent brain damage and physical malformation which would otherwise be caused by untreated intrauterine growth of the hydrocephalic fetus.

BRIEF DESCRIPTION OF THE DRAWINGS

Further objects and advantages of the invention will become apparent from the following description and claims, and from the accompanying drawings, wherein:

FIG. 7 is a diagrammatic view showing a system for calibration of the implant valve of the present invention.

FIG. 8 is an enlarged fragmentary elevational view, partly in cross-section, showing how the valve is secured in the calibration system of FIG. 7.

FIG. 9 is a diagrammatic view showing an apparatus for implanting a modified form of drainage valve according to the present invention.

FIG. 10 is an enlarged fragmentary vertical cross-sectional view taken through the implant tube of the apparatus of FIG. 9, showing how the drainage valve is positioned therein for implantation.

FIG. 11 is a horizontal cross-sectional view taken substantially on line 11—11 of FIG. 10.

FIG. 12 is a further enlarged horizontal cross-sectional view taken substantially on line 12—12 of FIG. 10.

FIG. 13 is a fragmentary vertical cross-sectional view taken substantially on line 13—13 of FIG. 12.

DETAILED DESCRIPTION OF PREFERRED EMBODIMENTS

Figure 1:
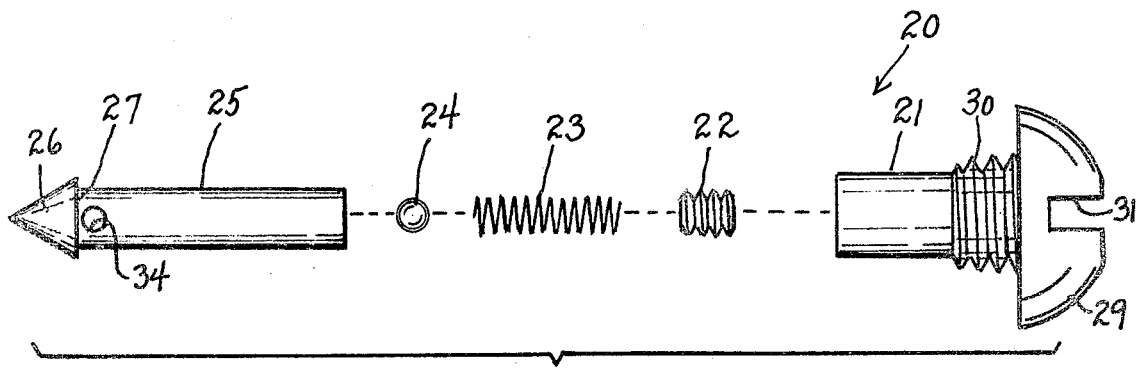
FIG. 1 is an exploded view of a hydrocephalus drain valve device in accordance with the present invention.
Figure 2:
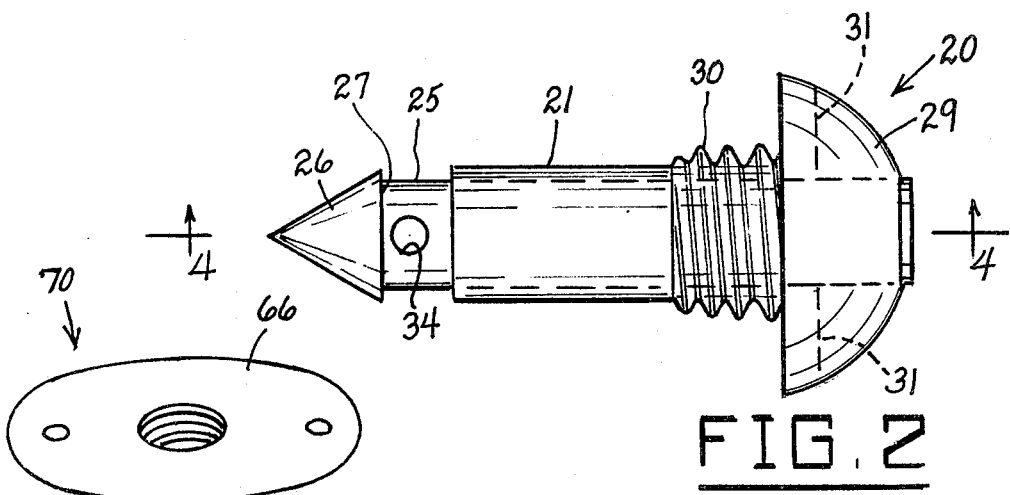
FIG. 2 is an enlarged elevational view of the assembled valve device of FIG. 1, shown in open position.

Referring to the drawings, and more particularly to FIGS. 1 to 6, a first typical embodiment of a pressure relief valve according to the present invention, called a "HAVIT" (meaning hydrocephalic antenatal vent for intrauterine treatment), is shown generally at 20. The relief valve device 20 is formed of five components, as best seen in FIG. 1, comprising a sleeve-like valve body 21, a hollow set screw 22, a coiled spring 23, a valve ball 24, and a valve element 25 in the form of a hollow shank having an enlarged solid integral conical tip 26 defining an annular shoulder 27. The parts 21, 22, 23 and 25 are all preferably fabricated from low carbon super alloy steel, such as Hastelloy C or 316 L stainless steel. The ball 24 is preferably fabricated from synthetic ruby, and typically is 0.047 inch in diameter. The hollow set screw 22 is hexagonally recessed at 28 (see FIGS. 4 and 11) for driving engagement by a conventional Allen wrench.

The sleeve-like valve body 21 is integrally formed with a spherically rounded head 29 and external implantation threads 30 adjacent said head. The head 29 has diametrically opposite radial grooves 31, 31 adapted to drivingly receive the spaced end prongs 32, 32 of a driving tool 33, shown in FIG. 6.

Figure 3:
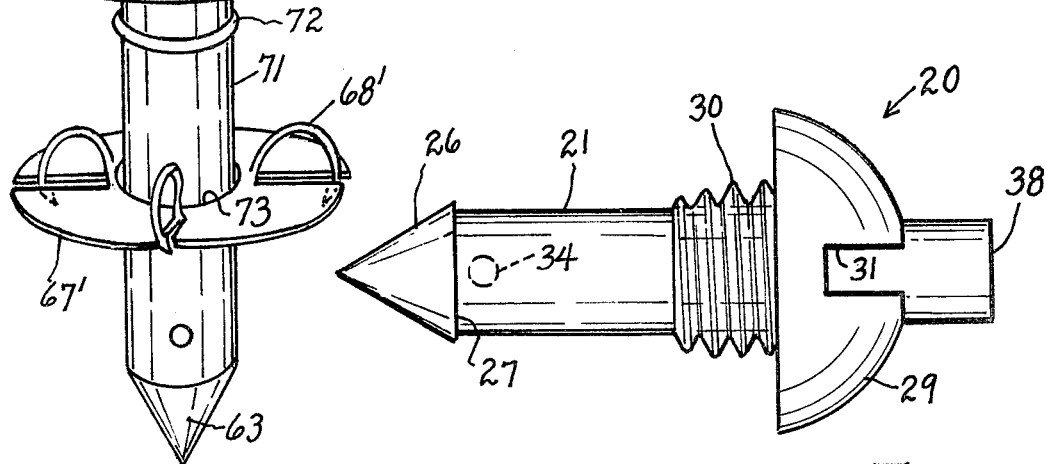
FIG. 3 is an enlarged elevational view of the assembled device of FIG. 1, shown in closed position.
Figure 4:
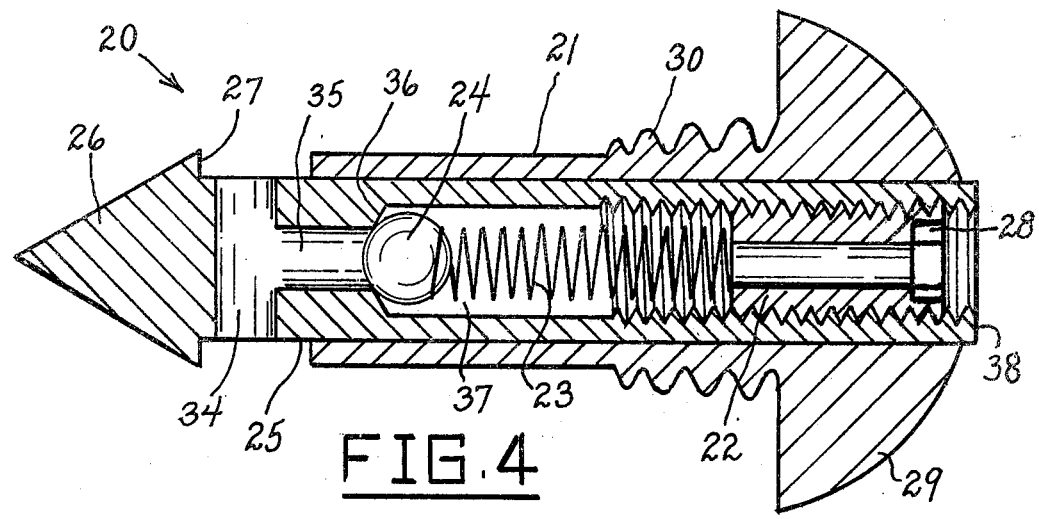
FIG. 4 is a further enlarged longitudinal cross-sectional view taken substantially on line 4—4 of FIG. 2.

As shown in FIG. 4, the shank member 25 is formed adjacent shoulder 27 with a transverse bore 34 which communicates with an axial bore 35 leading to an annular ball seat 36 in the hollow shank 25. The main axial cavity 37 contains the biasing spring 23, which bears between the valve ball 24 and the inner rim of set screw 22, which is threadedly engaged in cavity 37 and which is adjustable by means of an Allen wrench so as to vary the biasing force exerted by the spring 23 on the ball 24. The sleeve 21 is slidably engaged on the shank 25 and may be moved from a closed position thereon, as shown in FIG. 3, abutting the shoulder 27, to an open position shown in FIG. 2, by exerting a pushing inward axial force on the outer shank end 38, as will be presently described. When the valve assembly is in its open position, shown in FIGS. 2 and 4, a predetermined limiting hydrocephalic fluid pressure acting at passage 34 will unseat ball 24 and allow the fluid to flow out through the cavity 37 and the hollow set screw 22, thereby preventing the hydrocephalic pressure from rising above the preset limiting pressure value.

Referring to FIGS. 7 and 8, a typical calibration of the valve device 20 may comprise the following steps:

1. The shank assembly comprising the shank member 25 and the parts contained therein (the assembly of FIGS. 2, 3 and 4 with the sleeve member 21 removed) is inserted through the reduced end 39 of a transparent flexible tube 40 to the position shown in FIGS. 7 and 8, the reduced tube portion 39 being sufficiently resilient to allow the enlarged conical tip 26 to pass therethrough. The inside diameter of the main portion of tubing 40 is large enough to allow water pressure in the tube 40 to act freely on the transverse inlet bore 34.

2. The reduced tube portion 39 is sealingly clamped around shank 25 by means of a suitable clamp 41.

3. The opposite end of flexible tube 40 is suitably connected to one branch conduit 42 of a 3-way valve 43.

4. A syringe 44, filled with water, is connected to the inlet branch conduit 45 of the 3-way valve 43.

5. A manometer 46 is connected to the other conduit branch 47 of valve 43, via a small piece of tubing 48.

6. Using an Allen wrench engaged through the end 38 of shank 25, the set screw 22 is rotated counterclockwise to relieve the spring tension on ball 24. When no more spring tension can be felt on the set screw, the spring and ball are set free of tension.

7. The control lever 49 of 3-way valve 43 is turned to a position communicatively connecting branch 45 to branch 43 so that water will flow from the syringe 44 to the valve shank 25.

8. Water is injected from the syringe 44 into the shank 25 and is allowed to bleed through freely until no air bubbles can be seen in the transparent tube 40.

9. Using the Allen wrench, the set screw 22 is turned clockwise to close or tighten the ball 24 into its seat 36.

10. Lever 49 on 3-way valve 43 is turned to a position sealing off branch 42 (leading to tube 40 and shank 25) andd communicatively connecting branch 45 to branch 47, thereby connecting syringe 44 to manometer 46.

11. Water is injected by syringe 44 into manometer 46 to a pressure greater than the pressure setting desired for valve shank 25.

12. Lever 49 is then turned to a position shutting off the syringe 44 and communicatively connecting branch 47 to branch 42, thereby connecting manometer 46 to valve shank 25.

13. Using the Allen wrench, the implant valve shank 25 is slowly opened by turning the Allen wrench in a counterclockwise direction. As water starts to bleed out of the valve shank 25, the indicated pressure level in the manometer 46 will start to drop.

14. The spring tension in the valve shank 25 may then be adjusted to whatever pressure setting is desired.

To assure accurate pressure readings, the outlet end 38 of the implant valve shank 25 must be at the same level as the zero reading mark on the manometer 46 when calibrating.

Figure 5:
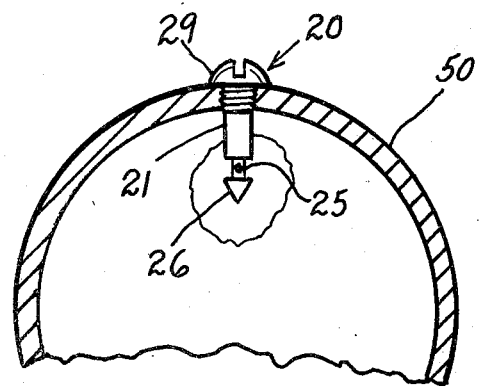
FIG. 5 is a schematic diagram showing the device of FIGS. 1 to 4 in operative position in the fetus, draining fluid directly to the uterus.
Figure 6:
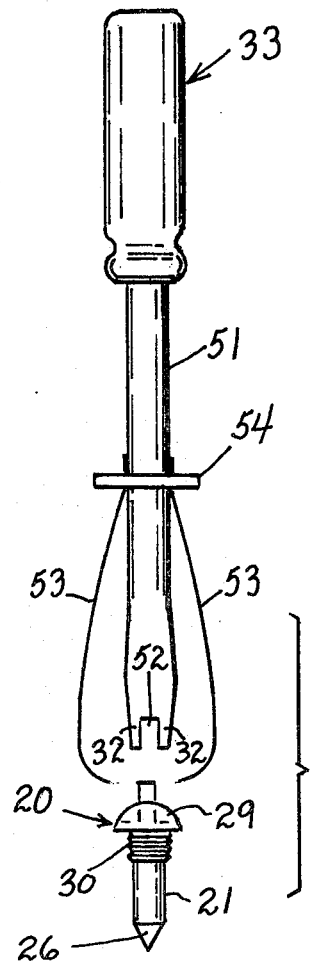
FIG. 6 is a schematic view of an insertion tool for a valve of the type shown in FIGS. 1 to 5, in accordance with the present invention.

As will be presently described, in the surgical placement of the relief valve device 20, the fetal head, shown at 50 in FIG. 5, is carefully exposed and punctured at a suitable chosen location, and the device 20 is inserted by threaded engagement in the puncture, using the insertion tool 33 of FIG. 6. The tool 33 has an elongated shank 51 formed with the spaced end prongs 32, 32 which are engaged in the radial grooves 31, 31, with the sleeve 21 in the closed position of FIG. 3, namely, abutting the shoulder 27. The top end of the shank 25 is received in the notch 52 defined between the prongs 32, 32. The tool 33 has opposing inwardly curved spring arms 53, 53 engageable beneath the head 29, the top ends of the spring arms being secured to the shank 51, and the shank being provided with a slidable locking ring 54 movable downwardly to releasably lock the arms 53, 53 in gripping positions. With the device 20 thus locked to the tool shank 51, the device 20 is engaged through the puncture and rotated to cause the threads 30 to bite into and threadedly interengage with the wall of the puncture, achieving the position substantially shown in FIG. 5. With this position achieved, the ring 54 is retracted, allowing the arms 53, 53 to spread and disengage from beneath the head 29. The top end of the shank 25 is then pushed downwardly to expose the intake passage 34, namely, to the open position of FIG. 2.

EXAMPLES

Manifestations of Hydrocephaly in Utero

Hydrocephaly was diagnosed prior to mid-gestation by following the course of abnormal ventricular dilation through sonographic images and maternal serum AFP. Upon reaching the 3rd trimester, hysterotomy provided nearly unrestricted accessibility to measure ventricular CSF pressures and perform surgical reparations. Whereas normal fetuses gave readings in the range of 45 to 55 mm of $H_2O$, hydrocephalus was sometimes associated with pressure of more than 100 mm of water. These definitive measurements were confirmed by visual symptoms, such as bulging of the eyes, retarded ossification of cranial sutures, and disproportionate enlargement of frontal aspects of the fetal skull. Frequently, the hydrocephaly caused protrusion of an encephalocele whenever crania bifidia was present.

Postnatal Outcome (Treated versus nontreated animals)

Untreated hydrocephalic neonates manifested intrauterine growth retardation (retarded 310 g±58, N=10; control 470 g±52, $\overline{X}$±SE) and usually died within 10 to 14 days after delivery; during this time they continued with severe hydrocephaly, progressive muscular weakness with delayed motor responses and frequent seizures accompanied by gastrointestinal and respiratory distress. In marked contrast, most infant monkeys that had been treated with the HAVIT in utero averted demise, demonstrated progressive physical dexterity and grew at near normal rates in the postnatal interval. Although their encephaloceles subsided in part, crania bifida remained, due to persistent hypoplasia of the occipital bones.

Procedures Applied to Intrauterine Placement of HAVIT

Access to the fetal cranium was obtained at hysterotomy between gestation 115–125 ( term=167 days) and the pathway of the HAVIT, relative to the lateral ventricles, was applied uniformly in all surgical procedures.

The surgery included:

(1) a ventral midline incision, extending from the umbilicus to the pubis and an incision 3–5 cm long made through the uterus and amnion over the head of the fetus and outside the limits of the placental girdle.

(2) Careful exposure of the fetal head was followed by puncture and placement of HAVIT in the cranial vault 3 mm lateral to the anterior fontanelle, with penetration 12–14 mm into the anterior horn of the ventricular cavity.

(3) The fetal head was placed back in the uterus. The amniotic sac was closed, when possible, with a simple continuous row of 3-0 Vicryl (Ethicon, Somerville, N.J.). The uterus was closed with a simple continuous row of 2-0 Vicryl and reinforced with a continuous Lambert suture. The abdominal wall was closed with simple interrupted sutures of 2-0 Vicryl. The skin edges were approximated with a continuous subcuticular suture and the skin closed with simple interrupted 2-0 Vicryl.

Roentgenographic observations followed the surgical insertion of the HAVIT. The security of the prosthesis in situ and the process of cranial configuration among hydrocephalic fetuses was monitored by X-ray at 4–6 week intervals until term.

FIG. 9 diagrammatically illustrates another system for implanting modified forms of drainage valves according to the present invention, shown in detail in FIGS. 10 to 13 and FIG. 14, respectively. The modified drainage valves are adapted to be implanted by employing a suitable fluid pressure source, such as a compressed air cylinder 54, to drive the valve into operative position in the fetal head 50 via a rigid guide tube 55 forming part of an insertion assembly, shown generally at 56. The assembly 56 includes a conventional fetoscope 57 optically coupled to the interior of the fetal head 50 via optical transmission means, such as fiber optic elements contained in a rigid tube 58 secured adjacent and parallel to the valve guide tube 55. The assembly 56 includes conventional solenoid valve means 59 controlled by a trigger switch 60 for opening the solenoid valve means to allow compressed air from tank 54 to be delivered to guide tube 55. The air pressure cylinder 54 and fetoscope 57 are commercially available.

The fetal head 50 is surgically positioned to permit the fetoscope to approach the anterior surface (mid-parietal area) with the guide tube perpendicular. The fetoscope 57 provides a means of viewing the cranial area into which the intake end of the drainage valve is to be introduced.

In the embodiment of FIGS. 10 to 13, the drainage valve, designated generally at 61, comprises a hollow shank member 62 with an inner cavity 37 and a ball valve element 24 on a valve seat 36 communicating with a transverse bore 34, and having an integral conical tip 63. A hollow set screw 22 is threadedly engaged in cavity 37 and bears on the top end of a coiled spring 64. Spring 64 has a reduced lower end portion 65 which bears on the valve ball 24. The tension of spring 64 can be adjusted by means of hollow set screw 22 in the same manner as described above, employing a calibration apparatus similar to that shown in FIGS. 7 and 8.

Shank 62 is provided with a suitably vented integral circular head 66 adapted to be positioned slidably in guide tube 55 and acting as a vented driving piston for the shank member 62.

Surrounding and slidably engaging shank member 62 is an implantation drivable washer member 67 provided with a plurality of evenly spaced peripheral straight depending barb elements 68 directed downwardly. The washer member 67 is slidable in the guide tube 55, said washer member 67 being drivingly engageable by the piston element 66 when it is driven downwardly by the compressed air from tank 54. The driving force causes the barbs 68 to penetrate the skin of the fetal head 50 and to lock the washer member 67 to the fetal head. Washer member 67 has a plurality of downwardly and inwardly inclined, evenly spaced, inner locking lugs 69 engaging shank member 62 (see FIG. 13) and locking the shank member in its downwardly driven position after the piston 66 has acted on the washer member 67 to drive the barbs 68 into the fetal skin. This secures the drain valve 61 in operative position in the fetal skull.

After the drain valve 61 has been implanted, its position can be optically checked by the fetoscope 57. The apparatus 56 can be thereafter disengaged, and the HAVIT remains secured to the skin over the ventricle until its removal sometime after birth.

The retaining water or ring 67 also serves to stabilize the movement of the HAVIT as it travels from within the tube 55 to its target.

Figure 14:
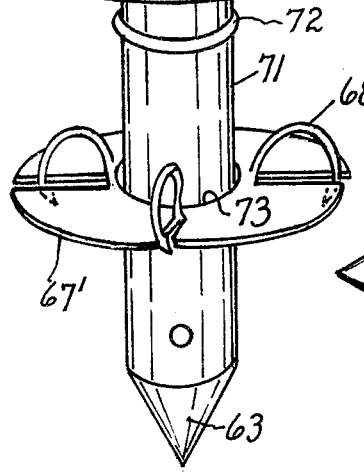
FIG. 14 is an enlarged perspective view showing a further modification of an implantable hydrocephalic drainage valve according to the present invention.

FIG. 14 illustrates another form of drainage valve, similar to that shown in FIGS. 10 to 13 and designated generally at 70. The valve assembly 70 comprises a shank member 71 generally similar to the previously described shank member 62 but having a peripheral locking rib 72 located subjacent to the integral piston element 66. The slidable locking washer, shown at 67', is formed at its peripheral portion with evenly spaced, integral resilient downwardly-directed barbed hook members 68' which are penetrable into the fetal skin in the same manner as barbs 68 in the embodiment of FIGS. 10 to 13, responsive to the downward driving force imparted by the piston member 66. When the shank 71 is driven downwardly, the peripheral rib 72 snaps past the inner central opening 73 of washer 67' and locks the shank 71 in its lowered position in the fetal skull, with the barbed hook members 68' embedded in the fetal skin, thus holding the drainage valve 70 in operative position. The drainage valve is removed sometime after birth.

As in the embodiment of FIGS. 10 to 13, the retaining washer or ring 67' also serves to stabilize the HAVIT 70 as it travels from within the tube 55 to its target.

While certain specific embodiments of improved hydrocephalic drainage valves have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A hydrocephalic drainage valve for in utero treatment of hydrocephalic fetuses comprising a hollow valve element shank with a pointed conical tip adapted to penetrate the skull of a fetus in utero, said shank having an intake port upwardly adjacent to said conical tip, a ball check valve in the hollow of said shank, spring means above said ball check valve and urging said ball check valve toward said intake port, a hollow set screw adjustably mounted in said shank above said spring means to vary the biasing force on said ball check valve, and means adjustable along said shank for operatively securing the shank in an implanted position in a fetal head with the intake port exposed in the cranial vault thereof whereby when fluid in the fetal cranium exceeds a predetermined amount, it drains therefrom through said drainage valve into the uterus.

2. The hydrocephalic drainage valve of claim 1, and wherein said spring means comprises a coiled spring bearing between said hollow set screw and said ball check valve.

3. The hydrocephalic drainage valve of claim 1, and wherein said shank is provided with means defining an enlarged head.

4. The hydrocephalic drainage valve of claim 1, and wherein said shank securing means comprises a valve sleeve body slidably engaged on said shank and having an enlarged head and having implantation screw threads subjacent said head.

5. The hydrocephalic drainage valve of claim 4, and wherein said conical tip is enlarged relative to the shank to define a shoulder limiting downward movement of the valve sleeve body with respect to said shank.

6. The hydrocephalic drainage valve of claim 1, and wherein said valve element shank is formed with an enlarged head and wherein said shank securing means comprises a washer member slidably mounted on the shank and having downwardly-directed skin-penetrating barb means, and means to substantially lock the washer member relative to the shank responsive to downward movement of the shank relative to the washer member.

7. The hydrocephalic drainage valve of claim 6, and wherein said means to substantially lock the washer member to the shank comprises peripheral rib means on the shank subjacent the head, the washer member being lockingly engageable with said rib means responsive to said downward movement of the shank relative to the washer member.

8. The hydrocephalic drainage valve of claim 6, and wherein said barb means comprises a plurality of spaced, downwardly-pointing hook-like arcuate resilient barbs on the peripheral portion of the washer member, said head being drivingly engageable with said arcuate resilient barbs responsive to downward movement of the shank relative to the washer member.

9. The hydrocephalic drainage valve of claim 6, and wherein said shank securing means comprises downwardly and inwardly-directed locking lug means on the inner periphery of the washer member engaging the shank, allowing downward movement of the shank relative to the washer member but locking the shank against subsequent upward movement relative to the washer member.

10. The hydrocephalic drainage valve of claim 1, and wherein said valve element shank is formed with an enlarged head and wherein said shank securing means comprises a washer member slidably mounted on said shank and having downwardly-directed skin-penetrating barb means, and means to substantially lock the washer member relative to the shank responsive to downward engagement of said head with said washer member.

11. The hydrocephalic drainage valve of claim 10, and wherein said barb means comprises a plurality of spaced depending substantially straight peripheral barbed lugs on the washer member.

12. The hydrocephalic drainage valve of claim 11, and wherein said means to substantially lock the washer member relative to the shank comprises downwardly and inwardly inclined lug means on the inner peripheral portion of the washer member, said lug means engaging the shank and allowing downward movement of the shank relative to the washer member but locking the shank against subsequent upward movement relative to the washer member.

13. The hydrocephalic drainage valve of claim 1, and wherein said valve element shank is formed with an enlarged head, wherein said shank securing means comprises a washer member slidably mounted on the shank and having downwardly-directed skin-penetrating barb means, and means to substantially lock the washer member relative to the shank responsive to downward movement of the shank relative to the washer member, and wherein said barb means comprises a plurality of spaced depending barbed lugs substantially vertically aligned with the periphery of said enlarged head.

14. The hydrocephalic drainage valve of claim 1, and wherein said valve element shank is formed with an enlarged head, wherein said shank securing means comprises a washer member slidably mounted on the shank and having downwardly-directed skin-penetrating barb means, and means to substantially lock the washer member relative to the shank responsive to downward movement of the shank relative to the washer member, and wherein said head and said washer member are substantially coaxially circular and of substantially the same diameter, enabling the head and the washer member to be slidably received in a common pneumatic driving tube and enabling the washer member to guide and stabilize the axial movement of the shank relative to such driving tube.

15. A drainage valve for in utero relief of pressure from hydrocephalic fluid in the cranial cavity of a fetus, comprising:

a hollow valve element including means, at one end, for penetrating said cranial cavity in utero, said valve element having an intake port adjacent said penetrating means and containing means for blocking flow of said fluid into said intake port and means for biasing said blocking means into blocking position;

and means, adjustably positioned on said valve element, for securing said valve element in an implanted position at said cranial cavity, wherein when pressure in said cranial cavity exceeds a predetermined amount, the force of said cavity pressure overcomes the force of the biasing means, said blocking means is moved to an unblocking position and said fluid flows into said intake port, through said valve element and out of the cranial cavity into the uterus.

* * * * *